United States Patent [19]

Eldridge, Jr. et al.

[11] 4,344,532
[45] Aug. 17, 1982

[54] SURGICAL BLADE REMOVER

[75] Inventors: John D. Eldridge, Jr., Balboa Island; Milton W. Cohen, Orange, both of Calif.

[73] Assignee: Instranetics, Inc., Tustin, Calif.

[21] Appl. No.: 177,123

[22] Filed: Aug. 11, 1980

[51] Int. Cl.³ .............................................. B65D 83/10
[52] U.S. Cl. .................................... 206/370; 206/355; 206/359; 206/363
[58] Field of Search ............... 206/352, 359, 354, 363, 206/370, 355, 356, 367, 370, 63.3

[56] References Cited

U.S. PATENT DOCUMENTS

| | | | |
|---|---|---|---|
| 3,244,317 | 4/1966 | Raybin | 206/355 |
| 3,438,484 | 4/1969 | Pinkas | 206/370 |
| 3,696,915 | 10/1972 | Douglas | 206/356 |
| 3,771,223 | 11/1973 | Danidowicz et al. | 206/354 |
| 3,941,243 | 3/1976 | Yamada | 206/356 |
| 4,011,944 | 3/1977 | Cooley et al. | 206/370 |
| 4,106,620 | 8/1978 | Brimmer et al. | 206/356 |
| 4,128,172 | 12/1978 | Joyce | 206/352 |
| 4,168,777 | 9/1979 | Gaskell et al. | 206/359 |
| 4,180,162 | 12/1979 | Magney | 206/356 |
| 4,182,448 | 1/1980 | Huck et al. | 206/63.3 |

Primary Examiner—Joseph Man-Fu Moy
Attorney, Agent, or Firm—Knobbe, Martens

[57] ABSTRACT

A surgical blade remover is disclosed having an essentially wedge-shaped support member which tapers from its front side to its back side. The support has one or more mutually parallel latitudinal slots open at one end and along their length extending from the front side of the support into its interior. The slots are sized to receive the tang of the blade holder while preventing the blade itself from passing therethrough. The surface of the support member bordering each slot is covered with an adhesive which holds the blade in place as the blade holder is pivoted downward in the slot away from the blade. When the hilt of the blade becomes detached from the holder, as a result of this pivoting action, the holder is withdrawn from the slot. The blade remains affixed to the adhesive on the support and is retained for its disposal.

19 Claims, 11 Drawing Figures

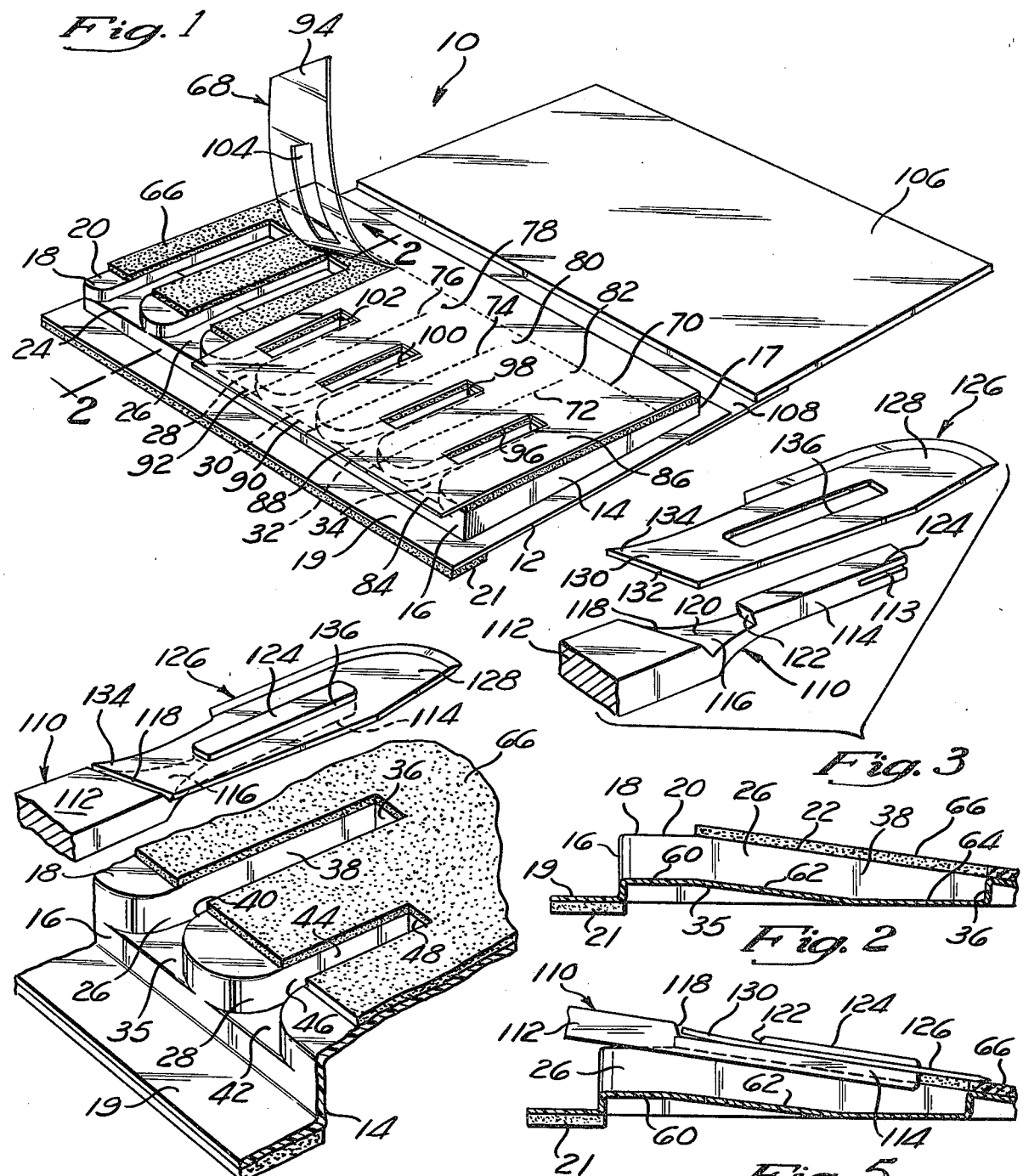

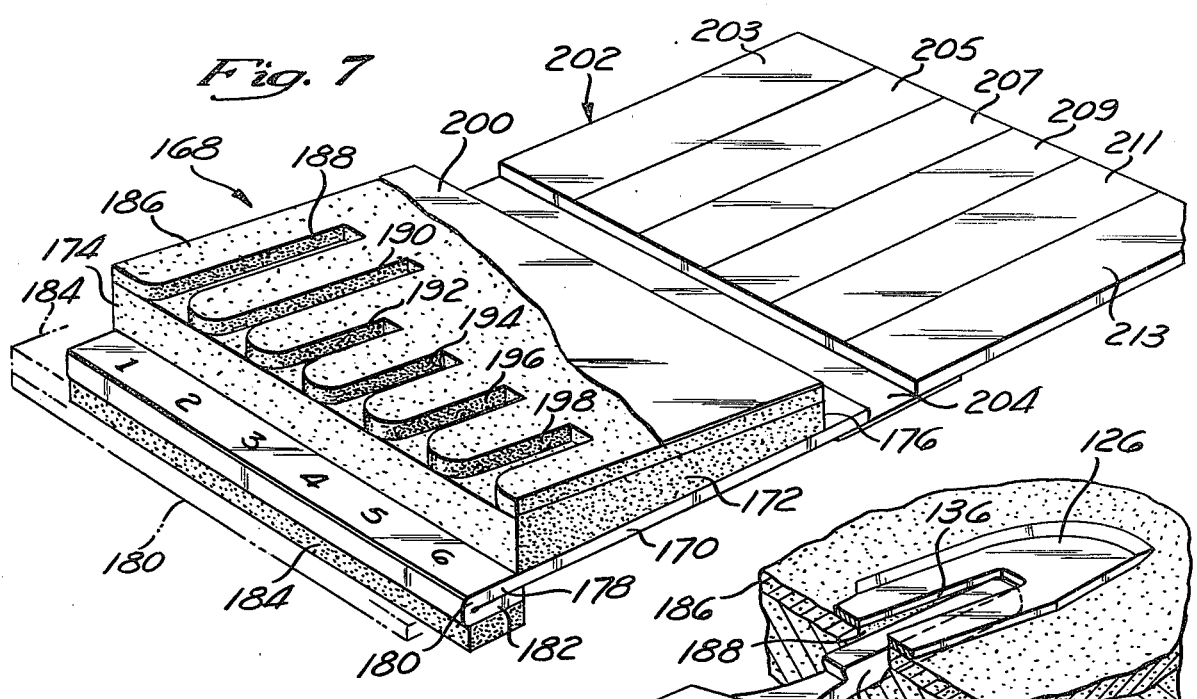
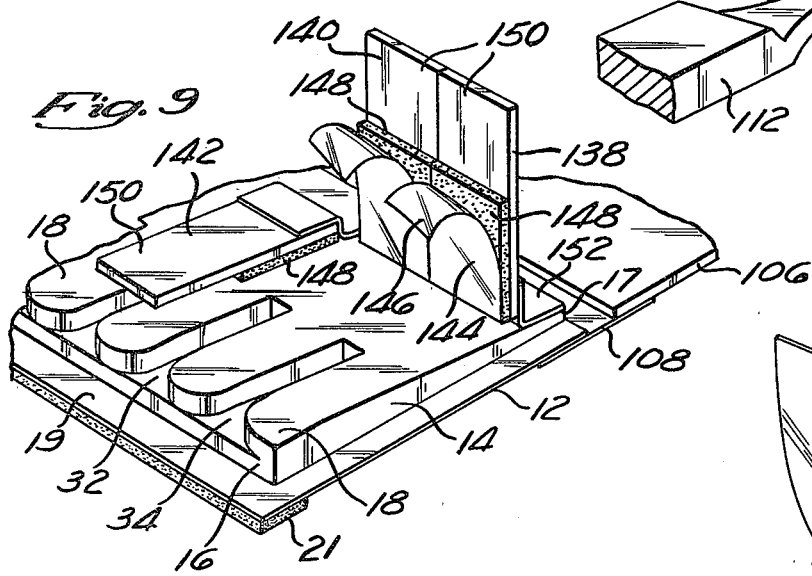
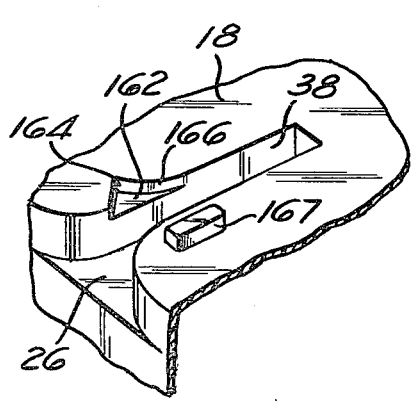
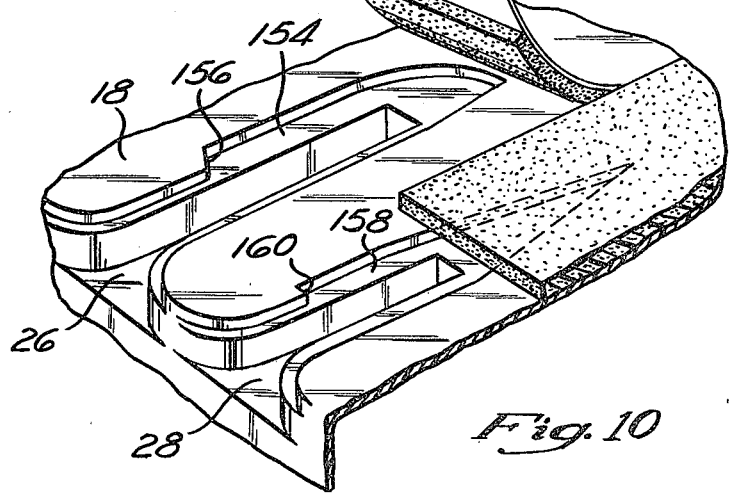

SURGICAL BLADE REMOVER

BACKGROUND OF THE INVENTION

The invention is directed toward devices for removing surgical blades from blade holders.

The scalpel, as a surgical implement, typically includes a handle having a tang with an upraised portion that mounts a replaceable blade. The handle, which can be resterilized, and is therefore reusable, is typically produced in one of two sizes, i.e., No. 3 or No. 4. The tang of a No. 3 handle is of a standard size to fit all sizes of the smaller dissecting blades used for internal incisions. Similarly, the tang of a No. 4 handle is of a standard size to fit all sizes of skin blades which are used to sever the skin in the initial incision. The width of the hilt of each of these surgical blades is fairly standard.

Each blade has a longitudinal opening cut therethrough which is adapted to slidably accommodate the upraised portion of the tang. When the tang is slidably positioned to project through the opening in the blade, the spring steel of the blade allows it to snap over the projection of the tang, locking the blade on the handle.

The blades are not reusable, and therefore must be safely and efficiently removed from the reusable handle. In order to remove the blade, the rearward portion of the blade adjacent the opening, i.e., the hilt, must be pried upward or distorted in order to clear the projection of the tang. In the past, the surgical nurse has often accomplished this task by using a forceps. With the tilt portion of the blade pried over the top of the projection, the blade is then held by an instrument, such as a forceps, and is slidably pulled off the handle tang. Such manual removal of the soiled blade is not only awkward, but also can be hazardous since the blade may carry viruses or other infectious disease.

At the conclusion of surgery, it is also important that all blades used be accounted for and discarded in a package which will not permit removed blades to fall out.

U.S. Pat. No. 4,120,397, issued to Neumann, represents an attempt to devise a blade remover which removes the blade and retains it in a receptacle which can then be discarded. The device, while perhaps an improvement over the manual forceps method, is not satisfactory since it is awkward and frustrating to manipulate. Even after fully understanding how the device is to be used, the blades are removed with difficulty. Moreover, the construction of the device is expensive, cumbersome and bulky.

There is therefore a definite need for a blade remover which quickly and safely removes the blade which is inexpensive and which retains the removed blade in a way that it can readily be accounted for and discarded.

SUMMARY OF THE INVENTION

The inventive surgical blade remover is formed of an essentially wedge-shaped support having a front which slopes down to a lower back portion. The support has a plurality of mutually parallel latitudinal slots which extend perpendicularly from the front edge of the support into its interior. The slots are open at their front end and along their length.

In the preferred embodiment, two slots are designed to remove the larger skin blades and four are designed to remove the smaller dissecting blades. Each slot has a width which is less than the width of the blade which it is designed to remove. Moreover, the length, depth, and width of each slot is sufficient to receive the tang of the particular handle attached to the blade to be removed.

The upper surface of the support is covered with an adhesive which borders each of the slots. A silicone treated paper is placed over the adhesive and is perforated to allow its removal from all slots at once or its selective removal from individual slots.

In order to remove a blade, one removes the peel-away paper from the slot to be used. This selective removal of the paper exposes a minimum surface area of adhesive, thereby decreasing the chance that the operator's gloves or clothing will become snagged. Next, the tang of the handle is inserted within the slot. Since the slot is narrower than the blade, the blade will lie flat against the adhesive surface of the support in overlapping fashion above the slot. The handle of the holder is then pivoted downward. Since the width of the slot is less than the width of the blade, the blade is not permitted to move downward with the handle. This causes the hilt portion of the blade to be pried upward until the opening in the blade clears the upraised projection of the tang. Once the hilt of the blade has cleared the tang projection, the handle is then withdrawn from the slot, slidably removing the handle tang from the blade. This removal is made possible by the adhesive which holds the blade in its fixed position against the surface of the support. The bladeless handle may then be resterilized for additional surgeries.

If desired, the slots may be numbered to provide a means for accurately accounting for the number of blades used. In a preferred embodiment, the support has an articulately connected cover which can be placed over the support to encase the blades which remain retained by the adhesive. The entire device can then be easily discarded without danger to hospital personnel.

The device therefore permits the easy and quick removal of surgical blades without requiring hospital personnel to physically contact the blades themselves. The adhesive not only allows for the easy extraction of the blade, but also retains the blade in its fixed position for safe and efficient accounting and disposal thereof.

Since the device is lightweight, compact, and inexpensive to produce, it is easy to manipulate in use and yet is economically disposable. Moreover, the device is capable of removing the various sizes of blades which are universally used.

In short, the device quickly and safely removes the various types of blades, provides an efficient and reliable system for identifying each blade, and simultaneously encapsulates the blades for their prompt and safe disposal.

DESCRIPTION OF THE DRAWINGS

These and other advantages will be clarified in the discussion below with reference to the following drawings in which:

FIG. 1 is a perspective view of a first embodiment of the inventive remover with its cover open and with the peel-away paper lifted to fully expose one slot;

FIG. 2 is a sectional view taken through line 2—2 of FIG. 1;

FIG. 3 is an exploded view showing the tang of the blade holder with a typical surgical blade aligned above the projection of the tang;

FIG. 4 is a fragmentary sectional view of a holder with attached blade positioned above a removal slot;

FIG. 5 is a sectional view, similar to that of FIG. 2, having the tang of the holder positioned within the slot and the attached blade resting on the surface of the support;

FIG. 6 is a sectional view, similar to that of FIG. 5, in which the blade holder has been pivoted downward to allow the hilt of the blade to clear the projection of the tang;

FIG. 7 is a perspective view of a second embodiment of the invention;

FIG. 8 is an enlarged fragmentary perspective view of the second embodiment with the tang of the holder inserted within a slot and being pivoted downward to detach the blade;

FIG. 9 is a fragmentary perspective view of an embodiment similar to that shown in FIG. 1, but having articulately connected flaps which pivot downward against the slot to keep the blade in its fixed position;

FIG. 10 is a fragmentary enlarged perspective view of a modified slot which is contoured to compliment the shape of the blade; and FIG. 11 is a fragmentary perspective view of a modified slot having a notch to receive a portion of the hilt of the blade to aid in the blade's removal.

DESCRIPTION OF THE PREFERRED EMBODIMENT

Referring to FIG. 1, a first embodiment of a blade remover 10 is shown. The removal 10 has a base 12 of a generally rectangular shape. The base 12 is advantageously made of a semi-rigid material, such as cardboard or the like, to provide support. Mounted on the base 12 is a generally wedge-shaped support member 14. The support 12 has a front side 16 which is parallel to a back side 17.

As most clearly shown in FIG. 2, the support 14 has an upper surface 18 which has a flat portion 20 that is essentially parallel to the base 12. The upper surface 18 then gradually slopes downward in a sloping portion 22. The front side 16 of the support 14 therefore represents the high portion of the wedge, while the back side 17 represents the low portion. The support 14 is advantageoudly formed of a rigid material, such as polystyrene.

The support 14 is somewhat smaller than the base 12 so as to leave a front portion 19 of the base which is not covered by the support 14. Attached to the underside of the front portion 19 is a strip of transfer tape 21. The tape 21 is advantageously covered with a peel-away silicone treated paper as is well known in the art. When the paper is removed, the tape 21 can be used to anchor the base 12 to a rigid support surface, such as a table, or table cover upon which the device 10 is to be used. Thus, the tape 21 prevents the device 10 from sliding or otherwise moving on the table surface when using the device 10.

Referring to FIGS. 1, 2, and 4, the support 14 has six slots 24, 26, 28, 30, 32, and 34, which extend from front side 16 into the interior of the support 14. Two of the slots 24,26 are sized to receive the larger tang of a handle for the larger skin blades whereas the remaining four slots 28,30,32,34 are sized to receive the smaller tang of a handle for the smaller dissecting blades.

As most clearly shown in FIG. 4, the slot 26 extends through the front side 16 of the support 14. The slot 26 is formed by a bottom surface 35, a back wall 36, and side walls 38 and 40. The slot 26 is therefore open at its end adjacent the front side 16 and is open along its entire length extending to the back wall 36. The side walls 38 and 40 are generally parallel to each other along the length of the slot 26 extending from the back side 36. However, at the open end of the slot 26, the side walls 38,40 diverge somewhat to create a larger opening. Referring to the sectional view of the slot 26, shown in FIG. 2, the bottom surface 35 of the slot 26 is formed of a relatively flat portion 60 that extends into a downwardly sloping portion 62 which extends into another relatively flat portion 64, terminating in the back wall 36.

In a like manner, the slot 28 is formed by a bottom surface 42, side walls 44,46, and a back wall 48. The side wall 44 of the slot 28 and the side wall 40 of the slot 26 merge with the front side 16 of the support 14 in a semi-circular pattern.

Affixed to the upper surface 18 is a layer of tape 66 which is covered with an adhesive on both its upper and lower surfaces. The tape 66 extends from the back side 17 almost up to the front side 16. The tape 66 therefore essentially borders each of the slots 24, 26, 28, 30, 32, and 34.

Affixed to the top of the tape 66 is a removable peel-away paper layer 68. The paper 68 extends from the back edge 17 of the support 14 past the front side 16 creating an overlapping portion 84. Advantageously, the under-surface of the paper 68, which contacts the tape 66, is treated with a non-adhesive material, such as silicone. This permits the paper 68 to be easily removed from the adhesive tape 66. The paper 68 has a longitudinal line of perforations 70. In addition, the paper 68 has a series of mutually parallel latitudinal lines of perforation located midway between each slot. It will be understood that in FIG. 1 the lines of perforation between the slots 24,26 and 26,28 are shown as already having been severed. The three remaining ones, 72, 74, and 76, extend from the front edge of the paper proximal to but not touching the longitudinal line of perforation 70. There is thus a series of small portions 78, 80, and 82 of the paper 68 which are not perforated between the longitudinal line of perforations 70 and the latitudinal perforations 72, 74, and 76.

The latitudinal perforations, such as 72, 74, and 76, form individual strips of paper 86, 88, 90, 92, and 94 which are centered over their respective slots. In FIG. 1, the strip located above the slot 24 has already been removed. Each of the strips 86, 88, 90, 92, and 94 has a rectangular opening 96, 98, 100, 102, and 104 which is approximately the width of each of their respective slots. If desired, the rectangular openings 96, 98, 100, 102, and 104 can extend forward through the overlapping portion of the paper 84 so that the full extent of each of the slots 24, 26, 28, 30, 32, and 34 is visible when the paper 68 covers the tape 66.

Articulately connected to the base 12 is a cover 106. The cover 106 is approximately the dimensions of the base 12 and is advantageously transparent. The cover 106 is attached to the base 12 by means of a strip of adhesive tape 108. The tape 108 is affixed to the under portions of the base 12 and the cover 106 in a book-binding type fashion to form a hinge. If desired, the base 12 and the cover 106 may be integrally formed and mutually folded to form an enclosure.

Referring to FIG. 3, an end portion of a blade holder 110, having a handle 112 with a forwardly extending tang 114, is shown. Located between the handle 112 and the tang 114 is a recess 116 which is formed by an angled longitudinal surface 118, a flat surface 120, and a vertical surface 122. The recess 116 forms an upraised projection 124 on the tang 114. The forward-most portion of the tang 114 has a longitudinal groove 113 which extends from the front edge of the tang about a third of its length on each side.

A blade 126 is shown having a forward cutting portion 128 and a rearward hilt portion 130. The blade 126 has a back edge 132 which is angled to abut the angled longitudinal surface 118 of the handle 112. The hilt portion 130 has a projecting point 134 which is directed toward the cutting direction of the blade. The blade 126 has a centrally located rectangular opening 136 extending therethrough. It will be understood that the blade holder 110 and the blade 126, as described, do not form a part of the invention, and are well known in the art.

In order to mount the blade 126 on the blade holder 110, the groove 113 on the tang 114 slidably engages the edges of the opening 136. The tang 114 is then slidably moved, with the aid of the groove 113, up to the forward-most portion of the opening 136. During this sliding process, the blade 126 is somewhat distorted from its planar configuration. As the upraised projection 124 of the tang 114 begins to fit within the opening 136, the hilt portion of the blade 130 snaps down into the recess 116. When the blade 126 is mounted, the hilt portion 130 rests against the flat surface 120 of the recess 116. Moreover, the back edge 132 of the blade 126 abuts the longitudinal surface 118 of a handle 112. The complimentary contour of the back edge 132 and the longitudinal surface 118 requires that when the blade 126 is correctly mounted, the cutting portion 128 will always be directed toward the left.

Referring to FIGS. 4, 5, and 6, the use of the slot 26 of the device 10 to remove the blade 126 will now be described. This description is exemplary of using any of the slots 24, 26, 28, 30, 32, or 34 to remove any type of surgical blade. The width of the slot 26 must be less than the width of the blade 126, but greater than the width of the tang 114. Moreover, the length of the slot 26 must be sufficient to accommodate the length of the tang 114. Finally, the depth of the slot 26, i.e., the height of the walls 38, 40, must be sufficient to accommodate the height of the tang 114 and prevent the handle tang 114 from interferring with the bottom surface 35 of the slot 26 when the handle 112 is pivoted to remove the blade. The slots 24, 26, 28, 30, 32, and 34 are of two basic sizes. The slots 24, 26 have a width less than the width of a skin blade and a width, length, and depth sufficient to accommodate the tang of a skin blade holder. Similarly, the slots 28, 30, 32, and 34 have a width slightly less than that of a dissecting blade, and a width, depth, and length sufficient to accommodate a dissecting blade holder. An approximate range of blade widths is from about $\frac{1}{8}$ inch for a dissecting blade to about $\frac{3}{4}$ inch for a skin blade. The range of tang sizes is from about $\frac{1}{2}$ inch $\times$ 1/16 inch (width) $\times$ 1/16 (height) for a No. 3 tang to about 1 inch (length) $\times \frac{1}{4}$ inch (width) $\times \frac{1}{4}$ (height) for a No. 4 tang. The size of the slots will be somewhat larger than the particular tang to provide adequate clearance.

In order to expose the adhesive surrounding the slot 26, the paper strip 94 is removed. In using the device 10, the operator may remove each individual paper strip 86, 88, 90, 92, or 94, as each respective slot is used. In this alternative, the surface area of tape 66, which is exposed, is kept to a minimum. This, therefore, helps prevent the operator's gloves or clothing from becoming snagged by the adhesive on the tape 66. Alternatively, the operator may remove all of the paper strips, i.e., 86, 88, 90, 92, or 94, by simply tearing the longitudingal line of perforation 70. The areas of imperforation, such as 78, 80, and 82, prevent the individual paper strips, such as 86, 88, 90, 92, from becoming detached before the entire line of strips is removed.

In the configuration, as shown in FIG. 1, the paper would normally be peeled away by pulling up against the front portion 84 of the paper 68. Alternatively, a longitudinal crimp can be made in the paper 66 adjacent the back edge 17. This forces the rearward-most portion of the paper 68 upward so that it may be conveniently grasped for removal.

The blade holder 110 is then inserted into the slot 26 with the projection 124 projecting upward. In this configuration, the cutting portion 128 will be facing to the left.

FIG. 5 shows the tang 114 inserted within the slot 26. In this position, the blade 126 rests against the adhesive 66 which borders the slot 26.

In order to remove the blade 126 from the tang 114, the handle 112 is pivoted downward within the slot 26. In this position, as shown in FIG. 6, the underside of the handle 112 will essentially rest against the flat surface portion 60 of the slot 26. Although the handle 112 pivots downward, since the blade 126 has a greater width than the slot 26, the blade remains affixed to the adhesive 66. The handle 112 is pivoted downward until the vertical surface 122 of the tang 114 no longer is engaged within or above the opening 136. With the vertical surface 122 of the tang 114 free of the blade 126, the handle 112 is slidably removed from the slot 26 in the direction shown by the arrow in FIG. 6. The tape 66 prevents the blade 126 from moving as the handle 112 is removed. In the entire blade removal process, the blade 126 is not touched by the operator. Thus, the device 10 provides an extremely safe mechanism to remove the surgical blades.

Once removed, the handle 112 can be reused. The blade 126 is retained in its fixed position on the tape 66. After each of the slots 24, 26, 28, 30, 32, and 34 has been used to remove a blade, the cover 106 can be placed over the tape 66 and the entire device 10 containing the removed blades can be disposed of. The device 10 therefore not only efficiently and safely removes the blades, but also provides a mechanism to retain and encase the blades after removal in a form in which they can be easily disposed of.

Advantageously, the front portion 19 of the base 12 can be printed so that each slot is numbered. This provides a system for strict accountability of each blade used and removed during a surgical procedure.

Referring to FIG. 9, an alternative embodiment for providing a means to hold the blade against the upper surface 18 of the support 14 is shown. Hingedly located along the rearward portion of the upper surface 18 is a series of multi-layered flaps 138, 140 and 142. Each of the flaps 138, 140, and 142 has a lower-most layer 144 which is formed of a peel-away paper whose upper side 146 is treated with a non-adhesive material, such as silicone. The middle layer of the flaps 138, 140, and 142 is a tape 148 having both sides covered with an adhesive similar to the tape 66, shown in the embodiment of FIG. 1. Affixed to the top surface of the tape 148 is a top layer 150 which is advantageously made of a more rigid material, such as polystyrene. It may be of a more flexible material, however, as shown in FIG. 10.

Each flap 138, 140, 142 is hingedly connected to the support 14 by means of a strip of tape 152 which runs longitudinally along the back side 17 of the support 14. The tape 152 allows the flaps 138, 140, 142 to be folded downward against the slots 24, 26, 28, 30, 32, 34. The length of the tape 148 is designed so that when the flap 138, 140, or 142 is folded downward, against its respective slot, the tape 148 will not cover any portion of the slot. This prevents the tape 148 from contacting the tang 114 of the handle 112. The paper 144 is then sized to cover the entire surface area of the tape 148. The top layer 150 of each flap 138, 140, or 142 is of a longer length than the tape 148. The longer length of the top layer 150 allows it to cover a much larger portion of the blade 126, including that portion which surrounds the upraised projection 124, when the blade holder 110 is inserted within one of the slots.

The use of the flap 138 will now be described. After a blade holder has been inserted within the slot 34, the peel-away paper 144 is removed from the tape 148. With the adhesive tape 148 exposed, the flap 138 is folded downward against the blade. Next, the blade handle will be pivoted downward to free the hilt portion of the blade from the upraised projection on the tang of the handle. The operator will then press down against the portion of the top layer 150 which covers the tape 148. Since the top layer 150 is composed of a rigid material, such as styrene, the operator's hand is protected from the blade itself. The blade handle is then withdrawn from the slot 34 and the blade is retained above the slot 34 by means of the tape 148.

Referring to FIG. 10, an alternative embodiment of the contour of the slots 24, 26, 28, 30, 32, and 34 is shown. As shown in FIG. 10, the upper surface 18, bordering the slot 26, has a recess 154 which is of the general shape of a skin blade. The recess 154 has a notch 156 which is shaped to compliment the most rearward portion of the cutting portion 128 of the blade 126. The function of the recess 154 is therefore two-fold. First, the recess 156 denotes to the operator the direction and precise position which the blade should take in the removal process. Secondly, the recess 154, and particularly the notch 156, serves to hold the blade in its position as the handle 112 is removed from the slot 26. Thus, in this modification, the use of adhesive tape, such as 66, or 148, may be eliminated. If desired, the flaps 138, 140, and 142, as shown in FIG. 9, may be used to further hold the blade in its fixed position above the slot. Again referring to FIG. 10, the upper surface 18 has a recess which borders the slot 28 and is shaped to compliment a dissecting blade. The recess 158 has a notch 160 which receives the most rearward portion of the cutting edge of a dissecting blade.

Referring to FIG. 11, the side wall 38 of the slot 26 is shown having a notch 162. The notch 162 is formed by cutting or forming a V-shaped recess into the upper surface 18 that borders the slot 26 along the side wall 38. The notch 162 has side surfaces 164 and 166. When the blade 126 is to be removed, the projecting point 134 is positioned within the notch 162. The surface 164 of the notch 162 abuts the back edge 132. When the handle 112 is removed from the slot 126, the surface 164 prevents the blade from moving outward with the handle.

As shown in FIG. 11, the upper surfce 18 may have an upraised rib 167 bordering the slot 26 at its oepn end to provide a pressure point against the lower surface of the hilt 130 of the blade 126 to increase the ease in removing the blade.

Referring to FIG. 7, an alternative embodiment 168 of the device is shown. The embodiment 168 has a base 170 which is generally rectangular in shape and is advantageously made of a material, such as cardboard or the like. The base 170 is thus quite similar to the base 12, as shown in FIG. 1. Affixed to the base 170 is a generally wedge-shaped support member 172. The support member 172 has a front side 174 and a back side 176 which are generally parallel.

The longitudinal length of the support 172 is about the same as that of the base 170. However, the width of the support 172 is smaller than the base 170 thereby leaving a front portion 178 of the base 170 which is exposed. The front portion 178 is, in turn, composed of a first section 180 and a second section 182. The first section 180, which is proximal to the support member 172, has imprinted thereon a sequential series of numbers for identifying the various blades removed as discussed above. The second section 182 is foldably connected to to the first section 180. Affixed to the upper surface of the second section 182 is a foam strip 184 which essentially covers the entire upper surface area of the second section 182.

Before the device 168 is used, the second section is in a relatively planar position with the first section 180 as shown in phantom in FIG. 7. However, when the device is to be used, the second section 182 is folded underneath the first section 180. In this position, the strip of foam 184 will rest against the surface upon which the device 158 is used, such as a table. The function of the foam strip 184 is to elevate the front portion of the support member 172. The foam strip 184 may provide a greater downward slope to the support member 172 from the front side 174 to the back side 176 and, in addition, allows the support member 172 to be formed in the shape of a rectangular box, if desired, as opposed to a wedge.

The support member 172 is advantageously formed of a foam, such as an open-celled styrofoam or polyethylene foam. Such a foam is somewhat compressible and yet still provides needed rigidity for the device 168. Alternatively, the support member 172 may be formed of a more rigid material such as styrene. Attached to the upper surface of the support member 172 is a second layer of foam 186. An adhesive is applied to the upper and lower surfaces of the layer 186. The layer 186 is advantageously composed of a foam which has a finer cell structure and is more compressible than the foam of the support member 172. Polyethylene has been found to be acceptable for the layer 186. Thus, it should be understood that the surface 172 and the layer 186 may be formed of a single layer of foam. Moreover, to add more rigidity, a layer of styrene may be interposed between the support 172 and the layer 186. Advantageously, the styrene layer overlaps the front side 174 of the support 172 to permit this overlapping portion to be folded down over the front side 174. The layer 186 has a series of latitudinal slots 188, 190, 192, 194, 196, and 198 which extend from the front side 174 of the support member 172 into the exterior of the device. The relative size and shape of each of the slots 188, 190, 192, 194, 196, and 198 is essentially identical to that of the slots 24, 26, 28, 30, 32, and 34, shown in FIG. 1. A sheet of peel-away paper 200, which can be treated with silicone, covers the foam layer 186. It should be understood that the paper layer 200 may take any of the forms as described for the embodiment shown in FIG. 1.

The device 168 has a cover 202 which is formed from a series of strips 203, 205, 207, 209, 211, and 213. The cover 202 is articulately connected to the underside of the base 170 by means of a strip of tape 204. The strips 203, 205, 207, 209, 211, and 213 are sized to cover the slots 188, 190, 192, 194, 196 and 198 respectively when the cover 202 is folded. Thus, when a scalpel with attached blade is positioned in one of the slots, the corresponding strip may be folded over the blade in a similar fashion to that described above for the top layer 150 shown in FIG. 9. The strips therefore protect the user's hand as the blade is moved. Moreover, the strips allow the user to selectively cover the adhesive surrounding each slot as each slot is used. Thus, the exposed tapes surrounding each slot can be immediately covered to prevent the adhesive from snagging gloves, clothing or the like.

The device 168 is used substantially in the same manner to remove blades as described above. Since the upper surface of the foam layer 186 is covered with an adhesive, the flaps 138, 140, and 142, as shown in FIG. 9, are not required. However, it should be understood that if desired, such flaps could be used in the configuration shown in FIG. 7. The contour of each of the slots 188, 190, 192, 194, 196, and 198 may also take any of the forms shown in FIGS. 10 and 11.

The embodiment shown in FIG. 7 has been found to be quite effective in removing surgical blades from their holders. The softness of the foam layer 186 allows the blade to make a slight depression therein which, in turn, aids in retaining the blade as the handle is detached. The support 172 which traverses each of the slots 188, 190, 192, 194, 196, and 198 offers a resistance to this blade depression thereby preventing the table upon which the device rests from interfering with the user's hand which is manipulating the blade holder as the blade is detached.

The depth of all slots, in all embodiments described thus far, is sufficient to receive the tang of the blade holder. However, with the embodiment shown in FIG. 7, the depth of the slot may be reduced. As shown in FIG. 8, the slot 188, in its normal state, is not of a sufficient depth to receive the entire tang 114 of the blade handle 112. However, since the foam support 172 is compressible, the operator, by placing a downward force on the tang 114, can depress the bottom surface of the slot thereby increasing the depth of the slot so that it may receive the tang 114. Thus, although in its normal state the slot 188 is not of a sufficient depth to receive the tang 114, it may be adapted to a sufficient depth. The depth of the slot 188, as shown in FIG. 8, is not the preferred depth since depressing the support 172 makes it somewhat more difficult to remove the blade.

It should also be understood that if desired, it may be possible to use a depressible material, such as a highly compressible foam, instead of the slots 188, 190, 192, 194, 196, and 198. That foam would have to have sufficient depressibility that upon compression, the slot formed is large enough to receive the tang of the blade holder.

It should also be understood that the supports 14 or 172 of any of the embodiments described above may be articulately connected to a hinged surgical instrument receptacle, as disclosed in applicant's pending application, Ser. No. 162,026, filed June 23, 1980, which is herein incorporated by reference. In this configuration, the covers 106 and 202 could be eliminated. The blade remover could be packaged within the receptacle, removed from the receptacle for use by pivoting the remover so that its base rests against the table, and pivoted back into the receptacle after use for disposal.

What is claimed is:

1. A device for removing a blade having an opening therethrough from a tang of a blade holder, said tang having an upraised projection which extends through said opening to mount said blade on said tang comprising:

a support surface for supporting a blade flat against said surface;

means defining an elongate channel open to said support surface and extending a substantial distance along said support surface, said channel being open at one end and having a width less than the width of said blade and more than the width of said tang, said channel being of sufficient depth to receive said tang with the end of said projection toward said channel open end disposed below said support surface while said blade is held flat against said support surface to permit said tang to be pressed down and pivoted away from said support surface and thereby released from said blade,; and means for holding the blade against said support surface when the tang is placed in said channel and pulled longitudinally relative to the blade out the open end of the channel after the blade is released from the tang but remains flat on said support surface.

2. A device suitable for placement on a rigid surface for removing a blade from a tang of a blade holder comprising:

a compressible sheet having front and back edges and upper and lower sides, said sheet having a latitudinal slot extending through the front edge of said sheet into its interior, said slot being open along the length thereof, said slot having a width greater than the width of said tang and less than the width of said blade;

a substrate fixed to the lower side of said sheet and transversing said slot, said substrate having a compressibility less than said sheet, said front edge of the sheet having a sufficient height and said substrate having a sufficient rigidity to allow said tang to be detached from said blade by pivoting the holder downward away from the blade without the rigid surface interferring with said pivoting holder;

means for holding the blade against said upper side of said sheet when the tang is placed within the slot and pulled longitudinally relative to the blade after the blade is released.

3. A device for removing a blade from a tang of a blade holder comprising:

a sheet having a planar top surface covered with an adhesive and a bottom surface, said sheet also having an elongate slot sized to receive said tang while preventing the face of said blade from passing therethrough; and a pad attached to said bottom surface of said sheet and supporting said sheet and blade against movement as said tang is pressed through said slot and removed longitudinally from said slot.

4. A device for removing a blade having an opening therethrough from a tang of a blade holder, said tang having an upraised projection which extends through said opening to mount said blade on said tang comprising:

a support having an essentially planar surface large enough to support the major portion of a blade flat on said support, said support having an elongate slot open at one end and its length extending from its open end at one side of the support into the interior of the support, said slot being of a depth adaptable to receiving said tang when the blade contacts said surface and to permit said tang to be pressed down and released from said blade while said blade remains flat on said surface, said slot having a width which is less than the width of the blade and more than the width of the tang; and means for holding the blade against said surface of the support when the tang is placed within the slot and pulled longitudinally relative to the blade after the blade is released.

5. A device for removing blades as defined in claim 4, further comprising:

a plurality of said slots having varying widths adapted to permit tangs of varying sizes to fit therein while preventing the blade attached to that tang from passing therethrough.

6. The device of claim 4 wherein said holding means is an adhesive covering the surface of said support bordering said slot.

7. The device of claim 4 wherein said holding means is a flap pivotably mounted to said support to fold against said support and over said blade when said tang is placed within said slot.

8. The device of claim 7 wherein said flap has adhesive applied to the side which contacts said blade.

9. The device of claim 5 wherein said slots are sequentially identifiable.

10. The device of claim 6 wherein said adhesive is covered with a removable non-adhesive material.

11. The device of claim 5 wherein said holding means is an adhesive covering the surface of said support bordering said slots.

12. The device of claim 11 wherein said adhesive is covered with a removable non-adhesive material.

13. The device of claim 12 wherein said removable material is selectively removable from each slot.

14. The device of claim 4 wherein a portion of said slot is contoured to compliment the shape of said blade.

15. The device of claim 4 wherein one side of said slot is notched near said open end, said notch shaped to receive a portion of the hilt of said blade to prevent said blade from moving with the holder as it is withdrawn from the slot.

16. The device of claims 4, or 5 further comprising means for forming an enclosure to encapsulate said blade after removal.

17. The device of claim 16 wherein said enclosure means comprises a cover articulately connected to said support to permit said cover and support to be foldable between a closed position and an open position, said cover being transparent to permit the visual inspection of removed blades when the cover and support are in the closed position.

18. The device of claim 4 wherein said support has an upraised rib bordering said slot proximal said open end, said rib being a pressure point against said blade when the tang is pressed down to release it from the blade.

19. The device of claim 5 further comprising a cover articulately connected to said support, said cover comprising a plurality of strips, each strip sized to selectively cover a removed blade retained on said support above said slots.

* * * * *